United States Patent [19]

King

[11] Patent Number: 5,965,625
[45] Date of Patent: Oct. 12, 1999

[54] COMPOSITIONS AND METHODS FOR THE CONTROL OF SMOKING

[76] Inventor: Michael Glenn King, RMD 531 Harbours Road, Yendon, Victoria 3352, Australia

[21] Appl. No.: 08/923,199

[22] Filed: Sep. 4, 1997

Related U.S. Application Data

[63] Continuation-in-part of application No. 08/809,400, Mar. 21, 1997, Pat. No. 5,883,137.
[51] Int. Cl.$^6$ .................................................. A61K 35/78
[52] U.S. Cl. ........................ 514/813; 424/195.1; 424/601; 514/532
[58] Field of Search ..................................... 514/813, 532; 424/195.1, 601

[56] References Cited

U.S. PATENT DOCUMENTS

| 4,305,942 | 12/1981 | Thiele et al. | 424/249 |
|---|---|---|---|
| 5,212,201 | 5/1993 | Wakashiro et al. | 514/532 |

FOREIGN PATENT DOCUMENTS

| 446119 | 2/1992 | Japan . |
|---|---|---|
| WO9609042 | 3/1996 | WIPO . |

*Primary Examiner*—James H. Reamer
*Attorney, Agent, or Firm*—Dann, Dorfman, Herrell and Skillman

[57] ABSTRACT

Compositions for the control of smoking are disclosed, the compositions comprising:

(a) an xanthine oxidase inhibitor;
(b) a phosphate or a compound capable of releasing phosphate on administration to a subject; and optionally
(c) a sugar; and still further optionally
(d) one or more pharmaceutically acceptable carriers or excipients.

There is also described methods for the control of smoking which comprises administering to a subject in need of such treatment the aforementioned composition.

20 Claims, No Drawings

COMPOSITIONS AND METHODS FOR THE CONTROL OF SMOKING

The present application is a continuation-in-part of U.S. patent application Ser. No. 08/809,400, filed Mar. 21, 1997, now U.S. Pat. No. 5,883,137.

This invention is directed to compositions and methods for use in the control of smoking, particularly the reduction in the desire to smoke.

There has generally been wide acceptance that smoking is a significant health risk. When smokers are compared to other members of the population, there is an increase in morbidity and mortality across all age groups. Smoking has been associated with asthma, emphysema, as well as cancerous conditions, such as of the mouth, larynx, tongue and lung. According Glynn and Sussman many smokers believe that smoking is a hazard to their health, yet despite this conviction a comparatively large percentage of people in Western and other populations continue to smoke (S. M. Glynn and S. Sussmann (1990) *Hospital and Community Psychiatry* 41(9): 1027–1028). Approaches for the control of smoking, such as hypnotism, acupuncture, "natural therapies" and nicotine-based interventions have met with little overall success. Established smokers generally find their habit very hard to give up.

In our copending application PCT/AU95/00621, we describe compositions and method for the control of smoking. We have very surprisingly found that compositions can be prepared which contain at a minimum two discrete classes of compounds which in combination are effective in reducing the desire of smokers to smoke, thus providing for the control of smoking.

In accordance with a first aspect of this invention there is provided a composition for the control of smoking, said composition comprising:

(a) an xanthine oxidase inhibitor;
(b) a phosphate or a compound capable of releasing phosphate on administration to a subject; and optionally
(c) a sugar; and still further optionally
(d) one or more pharmaceutically acceptable carriers or excipients.

In accordance with another aspect of this invention there is provided a method for the control of smoking, which comprises administering to a subject in need of such treatment a composition which comprises:

(a) an xanthine oxidase inhibitor;
(b) a phosphate or a compound capable of releasing phosphate on administration to a subject; and optionally
(c) a sugar; and still further optionally
(d) one or more pharmaceutically acceptable carriers or excipients.

In another aspect this invention relates to the use of a composition comprising:

(a) an xanthine oxidase inhibitor;
(b) a phosphate or a compound capable of releasing phosphate on administration to a subject; and optionally
(c) a sugar; and still further optionally
(d) one or more pharmaceutically acceptable carriers or excipients in the manufacture of a medicament for the control of smoking.

In a still further aspect of this invention there is provided agents for the control of smoking which comprise:

(a) an xanthine oxidase inhibitor;
(b) a phosphate or a compound capable of releasing phosphate on administration to a subject; and optionally
(c) a sugar; and still further optionally
(d) one or more pharmaceutically acceptable carriers or excipients.

The compositions and method according to this invention have surprisingly been found to control smoking. This is particularly surprising as it was previously regarded by the inventor that all of the components described in PCT/AU95/00621 i.e., a xanthine oxidase inhibitor; a cytochrome P450 inducing compound; a sugar; a source of phosphate; and, optionally, one or more pharmaceutical acceptable carriers or excipients) were necessary for the control of smoking. The control of smoking may result in a substantial reduction in the number of cigarettes smoked by in individual, or may result in the cessation of smoking. Various trials carried out with chronic smokers as described hereinafter show that the compositions of the invention suppress the desire or need to smoke.

Xanthine oxidase inhibitors block the activity of xanthine oxidase (including xanthine dehydrogenase and xanthine oxidoreductase) by a variety of mechanisms which include competitive inhibition (where the compounds act as an antagonist), binding to xanthine oxidase at or near the active site thereby blocking enzymic activity, altering the conformation of xanthine oxidase by binding to the xanthine oxidase enzyme generally outside of the active site, binding or otherwise inactivating free radical agents produced by xanthine oxidase, or other mechanisms. Xanthine oxidase inhibitors are well known in the art. Examples of xanthine oxidase inhibitors include plant extracts, such as from the plant *Eupatorium purpureum* (Gravel Root), allopurinol, oxypurinol, purpurogallin, and Trolox (a vitamin E analogue, for example as described by Zeng and Wu, 1992, *Cell Biol.* 70: 684–690).

One group of xanthine oxidase inhibitors are the flavonoids which may otherwise be referred to a bioflavonoids (see, for example, Harborne et al, (Eds), *The Flavonoids*, Academic Press, New York, 1975; Harborne et al, *The Flavonoids, Advances in Research Since* 1986, 1994; Princemail et al, (1987), 'Ginkgo Biloba extract inhibits oxygen species production generated by phorbol myristate acetate stimulated human leukocytes', *Experientia*, February 15 43(2), 181–184; Frage et al, (1987), 'Flavonoids as antioxidants evaluated in vitro and in situ liver chemiluminescence', *Biochem. Pharmacol.*, March 1 36(5): 717 720; Schmeda Hirschmann et al (1987), 'Preliminary pharmacological studies on *Eugenia uniflora* leaves: xanthine oxidase activity', *J. Ethnopharmacol.*, November 21(2) 183–186; Zeng L. H. and Wu T. W., (1992), 'Purpurogallin is a more powerful protector of kidney cells than Trolux and allopurinol', *Biochemistry and Cell Biology*, 70: 604–709; Siggins F. M., (1888), 'Analysis of the leaves of *Eupatorium purpurem*', *Am. J. of Pharm.*, 60: 121–122; Manger C. C., (1894), 'Euparin', *Am. J. of Pharm.*, 66: 120–124; Trimble H., (1890) '*Eupatorium purpurem*', *Am. J. of Pharm.*, February 62: 73–80).

The flavonoids are a large group of secondary plant metabolites derived from flavan. The basic structure of the flavanoids is flavanone (flavan-4-one) from which the flavonoid derivatives flavonol (flavan-3-ol), flavone and flavonol are derived. The anthocyanins and catechols are derived from flavan and are to be regarded for the purposes of this invention as flavanoids (see *Concise Encyclopedia of Chemistry*, de Gruyter, 1994, particularly pages 77, 190 and 411 to 413). Examples of anthocyanins include cyanin, pelargonin, delphin, idaein, malvin, petunin, keracyanin, micocyanin, frasarin, paeonin, oenin, and chyrsanthemin, and the like. These compounds may be hydrolyzed by acids and glycosidases to the corresponding aglycons (anthocyanins). Sugar residues may be bound 3- or 5-positions of the anthocyanins. Catechol tannins are a group of tannins in which the monomeric units are flavan-3-ol (catechols) or flavan-3,4-diol. Catechol is a 5,7,3',4'-tetrahydroxyflavan-3-ol. The above compounds are to be regarded as flavonoids for the purposes of this invention.

The most widely occurring flavonoids are the flavones. Flavones are yellow pigments of the flavonoid group which comprise the flavone, isoflavone or flavanone skeleton. Plavones occur widely in nature, for example, in blossoms, woods and roots, usually as glycosidses or esters of tannic acid and can be readily extracted from these natural sources, using long established techniques well known in the art such as those described in *The Flavonoids, Advances in Research Since* 1986, Harborne et al, 1994. Examples of flavones include apigenin, chrysin, eupatorin, fisetin, genistein, hesperitin, kaempherol, lutcolin, morin, myricetin and quercetin. Flavonoid compounds and other xanthine oxidase inhibitor within the scope of this invention may be extracted from a wide variety of plant species including *Eupatorium purpureum* (otherwise known as Gravel Root, Queen of the Meadow, or Jo Pyc Weed), *Eupatorium coenobium* (otherwise known as Agrimony), *Eupatorium fortunei* (the relevant extract being known as Peil lan, or Peilan) Ginkgo Biloba. Preferred examples are the compounds cuparin and eupatorin, or plant extracts containing these materials. Euparin containing extracts from *Eupatorium purpurem* are commercially available from a number of distributors, such as Blackmores 'Gravel Root Extract' (Blackmores Pty Ltd, Balgowlah, New South Wales, Australia). Flavonoids may be provided as plant extracts, prepared according to standard procedures in the art such as alcohol extraction.

Additional examples of flavonoid or bioflavonoids which may be used in this invention include citrus bioflavonoid, vitamin P, vitamin P complex, rutin, orange peel bioflavonoid, grapefruit peel bioflavonoid, lemon bioflavonoid, lime bioflavonoid, narigenin, naringin, naringenis, delphinidin, phloretin, cyanic, catechin, morin, phloridzin, phloretin, 3-hydroxyflavone, 3-deoxyflavonol, isorhamnetin, tricin, chrysoeriol, criodictyon, techtrochrysin, silybin, taxifolin, pinocembrim, galangin, robinin, diosmetin, kaempferide, rhamnetin and 3-O-methyl catechin.

Xanthine oxidase inhibitors may comprise plant extracts (for example, water and/or alcohol extracts) of plants such as *Eupatorlum purpurem* which have xanthine oxidase inhibitory activity, such as extracts from common tea, and extracts from oak bark or acorns.

Synthetically manufactured flavonoid compounds or analogues thereof, such as euparin which have xanthine oxidase inhibitory activity, are within the scope of this invention.

Other xanthine oxidase inhibitors which may be used in the invention include plant extracts with known demonstrable xanthine oxidase inhibitory activity such as modified tannins, extracts from common tea, and extracts from oak bark or acorns. Examples of other xanthine oxidase inhibitors include: purine analogues (such as caffeine, theobromine, theophylline, otofylline and the like); quinazolines (including methaqualone hydrochloride); triazines (such as 1,2,3-triazine, 1,3,5-triazine, cyanuric acid, cyanuric chloride and the like); pyrazalo (3,4-d)pyrimidines, such as, for example, allopurinol and oxypurinol; and benzocycloheptenones, such as, for example, purpurogallin.

Xanthine oxidase (XO) inhibitory activity can be readily assessed by standard biological assays, such as described in *Biochem. Biophys. Acta*. (1992) 1112(2): 178–182, which is incorporated herein by reference.

Compounds which bind or otherwise inactive free radicals produced by xanthine oxidase are to be regarded as inhibitors of xanthine oxidase. Such compounds include butylated hydroxyanisole, butylated hydroxytoluene, propyl gallate, sodium benzoate, pterins (*FEBS Lett* (1992) 304(2–3) 163–166), flavonoid compounds, superoxide dismutases, iron removing compounds such is desferrioxamine, glutathione, bilirubin, ubiquinones, plasma antioxidants such as albumin, water soluble antioxidants such as ascorbic acid, lipid soluble antioxidants such as the tocipherols, heme removing antioxidants such as haptoglobulin, zinc, magnesium, chromium, copper and manganese aspartates, and the like.

As mentioned above, xanthine oxidase inhibitors may be provided as plant/plant component extracts produced according to standard techniques in the art which are, for example described in the *British Herbal Pharmacopeia*, 1990 Volume 1, British Herbal Medicine Association, United Kingdom, and, *The Flavonoids, Advances in Research Since* 1986, Harborne et al, 1994.

Examples of a phosphate or a compound capable of releasing phosphate $PO_4^{3-}$) on administration to a subject include phosphoric acid, salts of orthophosphoric acid (which depending on the number of substituted hydrogen groups, may be primary phosphates, dihydrogen phosphates, secondary phosphates, hydrogen phosphates or tertiary phosphates including for example sodium, magnesium, and potassium salts, such as magnesium phosphate, sodium phosphate, potassium phosphate and the like), organic esters such as $C_{1-10}$ esters of phosphoric acid, and herbal extracts which liberate phosphate or phosphorous on administration to a human subject. Phosphates are to be regarded as including in scope organic phosphorous containing compounds including phytostigmine, minaprine and eserine. Preferably the compositions according to the present invention include one or more of such substances. For example, compositions according to one aspect of the invention may comprise an inorganic phosphorous containing compound such as magnesium phosphate, and an organophosphorous compound such as phytostigmine.

Optionally compositions of the present invention include a sugar such as fructose, sucrose, or any other sugars (whether monosaccharides, disaccharides or polysaccharides). Such sugar components may promote uric acid production in man. Examples of suitable sugars include glucose, fructose, galactose, xylose, arabinose, fucose, rhamnose, starch or other sugar containing polymers. Fructose is particularly preferred.

The compositions of the invention may comprise from about 0.1% to about 40% w/w, more specifically about 10% to 25% w/w/ of xanthine oxidase inhibitor; from about 0.2% to about 20%, more preferably about 0.5% to about 5% w/w and more specifically about 0.5% to about 4% w/w of a phosphate or a compound capable of releasing phosphate. The remainder of the compositions may comprise pharmaceutically acceptable carriers or excipients as described hereafter. Optionally, the compositions in an embodiment of the present invention additionally comprise a sugar, in an amount from about 10% to about 50% w/w, more specifically about 15% to about 40% w/w, still more specifically about 15% to about 30% w/w sugar.

The compositions according to this invention include those suitable for oral, topical (including buccal and sublingual), parenteral (including subcutaneous, intramuscular, intravenous, intraperitoneal and intradermal) vaginal or rectal administration or by implanting (for example, using slow release molecules). The compositions may conveniently be presented in the unit dosage form and may be prepared by any methods well known in the art of pharmacology. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Depending on the rate of administration, the active ingredients may be required to be coated in a material to protect the active ingredients from the action of enzymes, acids and other natural conditions which may inactivate the ingredients.

For oral administration, the pharmaceutical composition may be in the form of tablets, lozenges, pills, troches, capsules, elixirs, powders, granules, aqueous solutions, suspensions, emulsions, syrups and tinctures. Slow-release or delayed-release, forms may also be prepared, for example, in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange, or raspberry flavouring. Suitable coating agents include polymers or copolymers of acrylic acid and/or methyacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben, or sodium disulphate. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as described above or natural gums such as gum acacia or gum tragacanth.

For topical administration, the pharmaceutical composition may be in the form of a cream, ointment, gel, jelly, tincture, suspension or emulsion. The pharmaceutical composition may contain pharmaceutically acceptable binders, diluents, disintegrating agents, preservatives, lubricants, dispersing agents, suspending agents and/or emulsifying agents as described above.

The pharmaceutical forms suitable for parenteral administration include sterile aqueous solutions (where water soluble) or dispersions and powders for the extemporaneous preparation of sterile injectable solutions or dispersion. Pharmaceutical forms are stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol and liquid polyethylene glycol and the like), suitable mixtures thereof, and vegetable oils. Solutions or suspensions may further comprise one or more buffering agents. Suitable buffering agents include sodium acetate, sodium citrate, sodium borate or sodium tartrate. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, paraben, chlorobutanol, phenol, sorbic acid, thermerosal and the like. In many cases, it will be preferable to include isotonic agents, for example, sugars or sodium chloride. Prolonged absorption of the injectable compositions can be brought about, for example, by the use in the compositions of agents delaying absorption.

Sterile injectable solutions are prepared by incorporating the active ingredients in the required amounts amount in the appropriate solvent with various of the other ingredients enumerated above as required, followed by filtered sterilization.

Generally, dispersions are prepared by incorporating the various sterilized active ingredient or ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For rectal administration, the active ingredient is suitably administered in the form of an enema or suppository. A suitable suppository may be prepared by mixing the active ingredient with a non-irritating excipient which is solid at ordinary temperatures but which will melt in the rectum. Suitable such materials are cocoa butter and polyethylene glycols. Suitable enemas may comprise agents as described above with reference to forms for topical administration.

The above mentioned components used in formulating the active ingredients into suitable dosage forms may be collectively referred to as carriers and excipients.

The compositions according to this invention are preferably suitable for oral administration, more preferably as aqueous solutions. An example of a solution according to this invention may comprise:

(i) an aqueous/ethanol flavonoid extract, for example, extracted from the species *Eupatorium purpureum*;

(ii) an aqueous solution of a phosphate compound such as phosphoric acid; and (iii) flavouring.

In another embodiment the compositions may additionally comprise a sugar such as fructose.

According to the method of this invention the active ingredients may be administered separately, or alternatively as a composition containing each of the active ingredients, namely, a xanthine oxidase inhibitor, a phosphate or a compound capable of releasing phosphate, and optionally a sugar. In general, and without limiting the invention, a suitable dose of xanthine oxidase inhibitor will be in the range from 0.5 mg to 10 mg per kg body weight, preferably in the range of 3 mg to 6 mg per kg body weight per day, and more preferably in the range of 3 mg to 5 mg per kg body weight per day. In general, and without limiting the invention a suitable dosage range for the phosphate or a compound capable of releasing phosphate will be in the order of 0.01 mg to 0.5 mg per kg body weight per day, preferably in the range of 0.06 mg to 0.3 mg per kg body weight per day, and more preferably in the range of 0.08 mg to 0.25 mg per kg body weight per day. Where a sugar component is included in accordance with an optional embodiment of this invention, the sugar, such as fructose, may be present in an amount of 0.75 mg to 50 mg per kg body weight, preferably in the range of 4.5 mg to 30 mg per kg body weight per day, and more preferably in the range of 6 mg to 25 mg per kg body weight per day.

The respective components of the invention when in the form of a composition as described herein, may be administered from one to ten times per day, more preferably from one to five times per day, and administered at appropriate intervals and appropriate dosage levels. Administration may be maintained from one to ten weeks, preferably for at least two to four weeks.

The compositions of the invention may also have application in the treatment of fatigue, chronic tiredness, concentration difficulties, mood disturbance, or the general class of symptoms described as "asthenia" or "neurasthenia" or "post viral asthenia". Smokers may manifest one or more of these conditions which may result from various metabolic imbalances. A sign of such imbalance may be a strong urge to smoke. Treatment, or amelioration, of one or more of these conditions may result in a reduction of the urge or need to smoke.

The invention will now be described with reference to the following non-limiting examples.

EXAMPLE 1

The following active aqueous compositions were prepared:

| | |
|---|---|
| A) Ethanol extract (1:2 v/v) of the herb Gravel Root | 400 ml |
| Phosphate ions | 10 ml |
| Phosphoric acid | 10 g |
| or | |
| Calcium bi-phosphate | |
| Flavouring | 30 ml |
| Water | Making total volume up to 2 liters |

B) A composition according to A), additionally containing a thickening excipient (glucose syrup) in an amount of 1 kg.

C) A composition according to A), additionally containing 1 kg of fructose.

D) A composition according to A), additionally containing 1 kg glucose syrup and 1 kg fructose.

E) Compositions according to A) and D) wherein the gravel root extract is replaced with from 2 to 20 g of allopurinol, oxypurinol, purpurogallin or Trolox.

EXAMPLE 2

A series of clinical trails were conducted in Australia which demonstrated the effectiveness of the present invention in its various aspects. For conciseness certain details are set forth below:

A) Procedure

Participants in the trials were volunteers who, on average, smoked 30 or more cigarettes per day. Each trial lasted for six weeks with participants receiving daily the composition by oral administration. For the last two weeks of each trial no test composition or placebo composition was administered.

B) Composition

Compositions set out in Example 1 were orally administered in an amount of 10 ml per day.

In one trial there were the following treatment groups:

i) Group 1 who received composition D of Example 1.

ii) Group 2 who received a composition comprising:
   ethanol extract of Gravel Root
   glucose syrup
   flavouring
   water.

each of these components being present in amounts as per Example 1.

iii) Group 3 who received a composition comprising:
   fructose
   phosphoric acid
   flavouring
   glucose syrup
   water each of these components being present in amounts as per Example 1.

iv) Group 4 who received a composition comprising:
   ethanol extract of Gravel Root
   glucose syrup
   fructose
   flavouring
   water each of these components being present in amounts as per Example 1.

v) Group 5 who received composition A) of Example 1.

vi) Group 6 who received a composition comprising:

| | |
|---|---|
| flavouring | 30 ml |
| glucose syrup | 1 kg |
| water | to 2 liters |

C) Result

General

A small transient placebo effect was observed in group 6. No significant reduction in smoking during or after the trial was observed.

A major reduction in smoking rates by participants was observed in groups 1 and 5. However, a small number (less than about 10%) of participants were resistant to treatment, which in no way detracts from the effectiveness of the invention. In the other groups no significant effect on smoking was observed, that is, the treatment was ineffective.

Specific examples of the above are as follows:

Group 1

Mrs XAA was a woman in her late thirties who smoked more than 15 cigarettes per day. At the conclusion of the treatment program she had no desire to smoke.

Group 2

Mr XA was a 38 year old man who smoked 25 cigarettes per day. The treatment course had no effect.

Mr XB was a 46 year old man who smoked 40 cigarettes per day. The treatment course had no effect.

Group 3

Mr XC a middle aged man smoked over 30 cigarettes per day. The treatment course had no effect.

Group 4

Mr XD was a 46 year old man who smoked over 30 cigarettes per day. The treatment course had no effect.

Group 5

Mr XE was a 49 year old man who smoked 15 cigarettes per day. At the conclusion of the treatment course he had stopped smoking.

Mr XF was a 45 year old man who smoked 30 plus cigarettes per day. At the conclusion of the treatment program he had no desire to smoke.

Throughout this specification, unless the context requires otherwise, the work "comprise", or variations such as "comprises" or "comprising" or the term "includes" or variations thereof, will be understood to imply the inclusion of a stated element or integer or group of elements or integers but not the exclusion of any other element or integer or group of elements or integers. In this regard in construing the claim scope, an embodiment where one or more features is added to any claim is to be regarded as within the scope of the invention given that the essential features of the invention as claimed are included in such an embodiment.

I claim:

1. A composition for the control of smoking, said composition comprising:
   (a) an xanthine oxidase inhibitor;
   (b) a phosphate or a compound capable of releasing phosphate on administration to a subject; and optionally
   (c) a sugar; and still further optionally
   (d) one or more pharmaceutically acceptable carriers or excipients.

2. A composition according to claim 1, wherein said xanthine oxidase inhibitor is selected from a flavonoid, purine analogue, quinazoline, triazine, and pyrazalo(3,4-d) pyrimidine.

3. A composition according to claim 2, wherein said flavonoid is selected from a flavanone, flavonol, flavone, anthocyanin, catechol and catechol tannin.

4. A composition according to claim 2 wherein said flavonoid is in the form of an extract from a plant source containing one or more flavonoids.

5. A composition according to claim 1 wherein said xanthine oxidase inhibitor is an extract from a plant source.

6. A composition according to claim 5 wherein said plant source is *Eupatorium purpureum* (Gravel Root).

7. A composition according to claim 1, wherein said xanthine oxidase inhibitor is euparin.

8. A composition according to claim 1, wherein said xanthine oxidase inhibitor is selected from allopurinol, oxypurinol, purpurogallin and trolox.

9. A composition according to claim 1, wherein said phosphate, or a compound capable of releasing phosphate on administration to a subject, is phosphoric acid, a salt of phosphoric acid, an ester of phosphoric acid or herbal extracts which liberate phosphate.

10. A composition according to claim 9, wherein said source of phosphate is phosphoric acid, or a phosphate salt.

11. A composition according to claim 1, which includes a sugar wherein said sugar comprises fructose, sucrose, or a sugar which promotes uric acid production in man.

12. A method for the control of smoking, which comprises administering to a subject in need of such treatment a composition which comprises:
    (a) an xanthine oxidase inhibitor;
    (b) a phosphate or a compound capable of releasing phosphate on administration to a subject; and optionally
    (c) a sugar; and still further optionally
    (d) one or more pharmaceutically acceptable carriers or excipients.

13. A method for the control of smoking according to claim 12, wherein said xanthine oxidase inhibitor is selected from a flavonoid, purine analogue, quinazoline, triazine and pyrazalo (3,4-d)pyrimidine.

14. A method for the control of smoking according to claim 13, wherein said flavonoid is selected from a flavanone, flavonol, flavone, anthocyanin, catechol and catechol tannin.

15. A method for the control of smoking according to claim 12, wherein said xanthine oxidase inhibitor is an extract from a plant source.

16. A method for the control of smoking according to claim 15, wherein said plant source is Eupatorium purpureum.

17. A method for the control of the desire to smoke according to claim 12, wherein said xanthine oxidase inhibitor is euparin.

18. A method for the control of smoking according to claim 12, wherein said phosphate, or a compound capable of releasing phosphate on administration to a subject, is phosphoric acid, a salt of phosphoric acid, an ester of phosphoric acid or herbal extracts which liberate phosphate.

19. A method for the control of smoking according to claim 18, wherein said source of phosphate is phosphoric acid, or a phosphate salt.

20. The use of a composition comprising:
    (a) an xanthine oxidase inhibitor;
    (b) a phosphate or a compound capable of releasing phosphate on administration to a subject; and optionally
    (c) a sugar; and still further optionally
    (d) one or more pharmaceutically acceptable carriers or excipients in the manufacture of a medicament for the control of smoking.

* * * * *